(12) United States Patent
Guo et al.

(10) Patent No.: US 9,120,832 B2
(45) Date of Patent: Sep. 1, 2015

(54) METHYLTIN MERCAPTIDE DERIVATIVE AND METHOD FOR PREPARING THE SAME

(71) Applicant: Yunnan Tin Company Limited, Gejiu (CN)

(72) Inventors: Yinghui Guo, Gejiu (CN); Laoyong Yan, Gejiu (CN); Baoliang Zhao, Gejiu (CN); Qiangshun Yi, Gejiu (CN); Bing Wei, Gejiu (CN); Xiangyan Li, Gejiu (CN); Shu Chen, Gejiu (CN); Fuliang Duan, Gejiu (CN)

(73) Assignee: YUNNAN TIN COMPANY LIMITED, Gejiu (CN)

( * ) Notice: Subject to any disclaimer, the term of this patent is extended or adjusted under 35 U.S.C. 154(b) by 0 days.

(21) Appl. No.: 14/270,347

(22) Filed: May 5, 2014

(65) Prior Publication Data
US 2014/0357883 A1    Dec. 4, 2014

(30) Foreign Application Priority Data

May 29, 2013   (CN) .......................... 2013 1 0208211

(51) Int. Cl.
*C07F 7/22*    (2006.01)
(52) U.S. Cl.
CPC .................... *C07F 7/2268* (2013.01)
(58) Field of Classification Search
CPC ..................................... C07F 7/2268
USPC ............................................. 556/93
See application file for complete search history.

(56) References Cited

U.S. PATENT DOCUMENTS 3,925,309 A  *  12/1975  Weisfeld et al. ............. 524/180

OTHER PUBLICATIONS

Bacaloglu et al., Annual Technical Conference—Society of Plastics Engineers, 57th (vol. 3), pp. 3564-3568 (1999).*

* cited by examiner

*Primary Examiner* — Porfiro Nazario Gonzalez
(74) *Attorney, Agent, or Firm* — Matthias Scholl P.C.; Matthias Scholl

(57) ABSTRACT

A compound represented by formula I or II and a method for preparing the same. The method includes: a) adding isooctyl mercaptopropionate to a reactor, adding dropwise an aqueous solution of methyltin chloride, stirring and allowing for a complete reaction, and adding aqueous ammonia, an aqueous solution of sodium hydroxide, an aqueous solution of sodium bicarbonate, an aqueous solution of sodium carbonate, or a solution of an organic base to regulate the pH value of a resulting mixture from a starting value of between 2 and 8 to an end value of between 6 and 10 for a primary stage of esterification; and b) allowing a product obtained from step a) to proceed to a secondary stage of the esterification, allowing the product to stand until phases are separated, collecting and washing an organic phase using deionized water, allowing a resulting mixture to stand until phases are separated.

5 Claims, No Drawings

METHYLTIN MERCAPTIDE DERIVATIVE AND METHOD FOR PREPARING THE SAME

CROSS-REFERENCE TO RELATED APPLICATIONS

Pursuant to 35 U.S.C. §119 and the Paris Convention Treaty, this application claims the benefit of Chinese Patent Application No. 201310208211.X filed May 29, 2013, the contents of which, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

The invention relates to a methyltin mercaptide derivative having a high boiling point and a method for preparing the same.

2. Description of the Related Art

Organotin is an important heat stabilizer in plastics processing, and generally presents as a derivative of a laurate, maleate, or mercaptan.

As one of the most widely used heat stabilizers, methyltin mercaptides represented by formula III or IV have a low boiling point and high volatility. Thus, when used in the process of calendering at high temperature and high rotational speed, the heat stabilizer is easily volatile thereby lowering the reactivity.

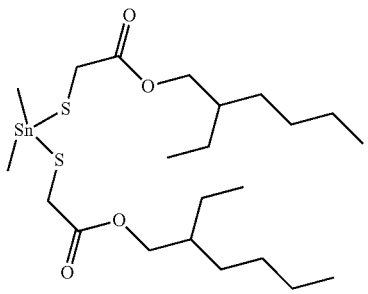

IV

SUMMARY OF THE INVENTION

In view of the above-described problems, it is one objective of the invention to provide a methyltin mercaptide derivative and a method for preparing the same. The methyltin mercaptide derivative has a high boiling point and chemical properties similar to conventional methyltin isooctyl thioglycolates, and thus is suitable for use in the process of calendering at high temperature and high rotational speed.

To achieve the above objective, in accordance with one embodiment of the invention, there is provided a compound represented by formula I or II:

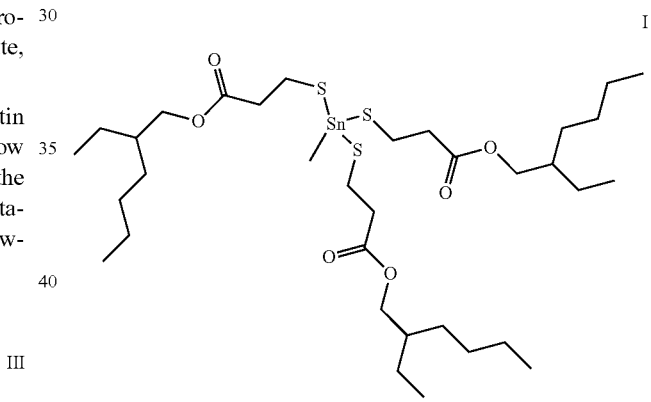

I

II

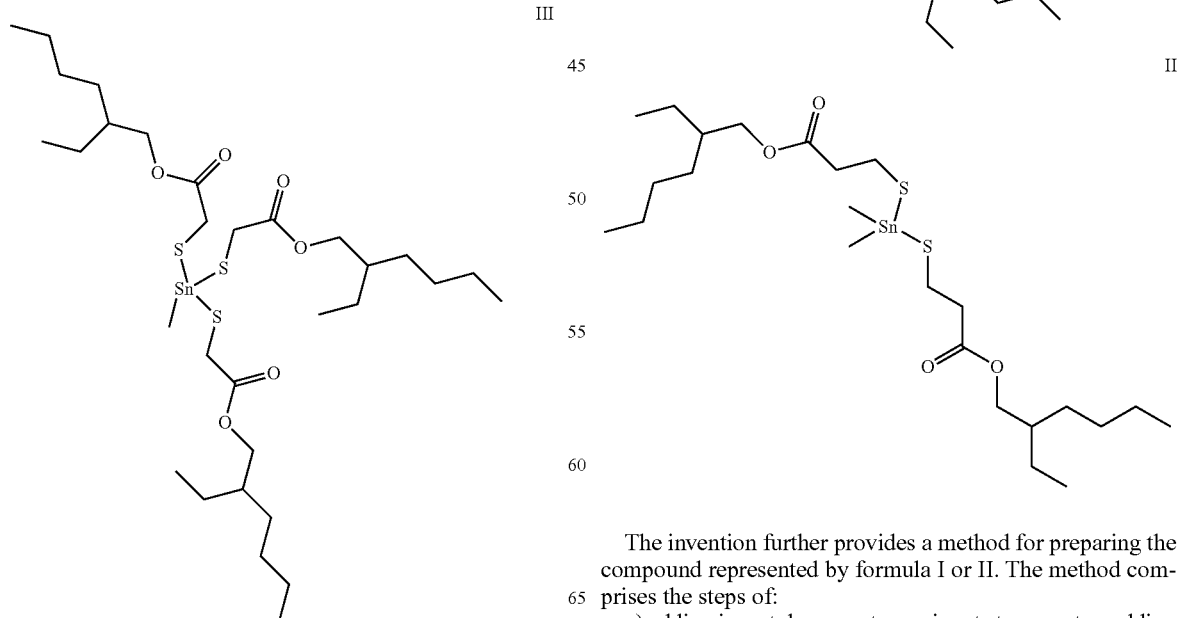

III

The invention further provides a method for preparing the compound represented by formula I or II. The method comprises the steps of:

a) adding isooctyl mercaptopropionate to a reactor, adding dropwise an aqueous solution of methyltin chloride, stirring and allowing for a complete reaction, and adding aqueous ammonia, an aqueous solution of sodium hydroxide, an aqueous solution of sodium bicarbonate, an aqueous solution of sodium carbonate, or a solution of an organic base to regulate the pH value of a resulting mixture from a starting value of between 2 and 8 to an end value of between 6 and 10 for a primary stage of esterification;

b) allowing a product obtained from step a) to proceed to a secondary stage of the esterification, allowing the product to stand until phases are separated, collecting and washing an organic phase using deionized water, allowing a resulting mixture to stand until phases are separated, and filtering; and c) collecting an organic product obtained from step b), and evaporating the product under reduced pressure to yield the compound.

In a class of this embodiment, in the primary stage of the esterification, a molar ratio of chloride in the methyltin chloride aqueous solution to the isooctyl mercaptopropionate is between 1:1.0 and 1:1.2.

In a class of this embodiment, in the primary stage of the esterification, a reaction temperature is controlled at between 10 and 40° C.

In a class of this embodiment, in the secondary stage of the esterification, a reaction temperature is controlled at between 40 and 80° C.

In a class of this embodiment, a reaction temperature for the evaporation under reduced pressure is controlled at between 60 and 140° C.

Advantages according to embodiments of the invention are summarized below. The methyltin chloride aqueous solution is added dropwise to isooctyl mercaptopropionate for synthetic reaction thereby weakening the formation of acid mist and inhibiting the side reaction, and the yield is up to 96%. The prepared compound has a high boiling point, can take the place of conventional methyltin isooctyl thioglycolates, and is suitable for use in the process of calendering at high temperature and high rotational speed. The compound is more environmentally friendly, safe, and high efficient in reactivity.

DETAILED DESCRIPTION OF THE EMBODIMENTS

For further illustrating the invention, experiments detailing a methyltin mercaptide derivative having a high boiling point and a method for preparing the same are described below. It should be noted that the following examples are intended to describe and not to limit the invention.

In the invention, based on the reaction conditions and the reaction sequence, the esterification comprises a primary stage and a secondary stage. In the primary stage, the temperature is between 10 and 40° C., and a starting pH value is controlled at between 2 and 8 and an end pH value at between 6 and 10. Isooctyl mercaptopropionate is substituted for the chloride in the methyltin chloride aqueous solution to yield a crude product of a methyltin mercaptide derivative which has a high boiling point. Due to high concentrations of the reactive materials, to control the primary stage of the esterification at a relatively low temperature can prevent the side reaction.

As a supplement to the primary stage, the secondary stage of the esterification is controlled at a relatively high temperature of between 40 and 80° C. and at a pH value of between 6 and 10. Under a relatively high temperature and pH value, the crude product continues to react whereby improving the yield of the target product.

Example 1

301.1 g of isooctyl mercaptopropionate was added to a reactor and stirred. 300 g of methyltin chloride aqueous solution comprising 16.0 wt. % of chloride was added dropwise. The pH value of the resulting mixture was regulated using a sodium bicarbonate solution to be between 2 and 4. The temperature was controlled at between 10 and 20° C. Thereafter, the sodium bicarbonate solution was further added dropwise to regulate the pH value to be 7, and thus the primary stage of the esterification occurred. The temperature was raised to between 40 and 60° C. for the secondary stage of the esterification. Thereafter, the mixture was allowed to stand until phases separated. The aqueous phase was removed. The organic phase was washed with 320 g of deionized water. The resulting solution was allowed to stand until phases separated. The obtained organic product was filtered, and evaporated under reduced pressure at a temperature of between 120 and 140° C. whereby removing water. Thus, 382.1 g of a colorless transparent liquid comprising 18.0 wt. % of tin was obtained, with a yield of 98%. The colorless transparent liquid was a methyltin mercaptide derivative having a high boiling point.

Example 2

291.6 g of isooctyl mercaptopropionate was added to a reactor and stirred. 300 g of methyltin chloride aqueous solution comprising 15.2 wt. % of chloride was added dropwise. The pH value of the resulting mixture was regulated using a sodium hydroxide solution to be between 4 and 6. The temperature was controlled at between 20 and 30° C. Thereafter, the sodium hydroxide solution was further added dropwise to regulate the pH value to be 6, and thus the primary stage of the esterification occurred. The temperature was raised to between 45 and 55° C. for the secondary stage of the esterification. Thereafter, the mixture was allowed to stand until phases separated. The aqueous phase was removed. The organic phase was washed with 300 g of deionized water. The resulting solution was allowed to stand until phases separated. The obtained organic product was filtered, and evaporated under reduced pressure at a temperature of between 70 and 90° C. whereby removing water. Thus, 365.4 g of a colorless transparent liquid comprising 16.9 wt. % of tin was obtained, with a yield of 97.2%. The colorless transparent liquid was a methyltin mercaptide derivative having a high boiling point.

Example 3

318.3 g of isooctyl mercaptopropionate was added to a reactor and stirred. 350 g of methyltin chloride aqueous solution comprising 14.5 wt. % of chloride was added dropwise. The pH value of the resulting mixture was regulated using a sodium carbonate solution to be between 6 and 8. The temperature was controlled at between 15 and 25° C. Thereafter, the sodium carbonate solution was further added dropwise to regulate the pH value to be 9, and thus the primary stage of the esterification occurred. The temperature was raised to between 50 and 70° C. for the secondary stage of the esterification. Thereafter, the mixture was allowed to stand until phases separated. The aqueous phase was removed. The organic phase was washed with 320 g of deionized water. The resulting solution was allowed to stand until phases separated. The obtained organic product was filtered, and evaporated under reduced pressure at a temperature of between 90 and 110° C. whereby removing water. Thus, 406 g of a colorless transparent liquid comprising 15.8 wt. % of tin was obtained, with a yield of 98.5%. The colorless transparent liquid was a methyltin mercaptide derivative having a high boiling point.

Example 4

260.9 g of isooctyl mercaptopropionate was added to a reactor and stirred. 250 g of methyltin chloride aqueous solution comprising 16.8 wt. % of chloride was added dropwise. The pH value of the resulting mixture was regulated using aqueous ammonia to be between 3 and 5. The temperature was controlled at between 20 and 30° C. Thereafter, aqueous ammonia was further added dropwise to regulate the pH value to be 9, and thus the primary stage of the esterification occurred. The temperature was raised to between 40 and 60° C. for the secondary stage of the esterification. Thereafter, the mixture was allowed to stand until phases separated. The aqueous phase was removed. The organic phase was washed with 260 g of deionized water. The resulting solution was allowed to stand until phases separated. The obtained organic product was filtered, and evaporated under reduced pressure at a temperature of between 80 and 100° C. whereby removing water. Thus, 336.9 g of a colorless transparent liquid comprising 18.3 wt. % of tin was obtained, with a yield of 99.5%. The colorless transparent liquid was a methyltin mercaptide derivative having a high boiling point.

Example 5

287.8 g of isooctyl mercaptopropionate was added to a reactor and stirred. 300 g of methyltin chloride aqueous solution comprising 15.6 wt. % of chloride was added dropwise. The pH value of the resulting mixture was regulated using an organic base solution to be between 5 and 7. The temperature was controlled at between 30 and 40° C. Thereafter, the organic base solution was further added dropwise to regulate the pH value to be 8, and thus the primary stage of the esterification occurred. The temperature was raised to between 40 and 60° C. for the secondary stage of the esterification. Thereafter, the mixture was allowed to stand until phases separated. The aqueous phase was removed. The organic phase was washed with 300 g of deionized water. The resulting solution was allowed to stand until phases separated. The obtained organic product was filtered, and evaporated under reduced pressure at a temperature of between 100 and 120° C. whereby removing water. Thus, 368.8 g of a colorless transparent liquid comprising 17.1 wt. % of tin was obtained, with a yield of 98.5%. The colorless transparent liquid was a methyltin mercaptide derivative having a high boiling point.

Example 6

303.7 g of isooctyl mercaptopropionate was added to a reactor and stirred. 350 g of methyltin chloride aqueous solution comprising 13.7 wt. % of chloride was added dropwise. The pH value of the resulting mixture was regulated using aqueous ammonia to be between 4 and 6. The temperature was controlled at between 25 and 35° C. Thereafter, aqueous ammonia was further added dropwise to regulate the pH value to be 10, and thus the primary stage of the esterification occurred. The temperature was raised to between 60 and 80° C. for the secondary stage of the esterification. Thereafter, the mixture was allowed to stand until phases separated. The aqueous phase was removed. The organic phase was washed with 310 g of deionized water. The resulting solution was allowed to stand until phases separated. The obtained organic product was filtered, and evaporated under reduced pressure at a temperature of between 60 and 80° C. whereby removing water. Thus, 380.6 g of a colorless transparent liquid comprising 17.7 wt. % of tin was obtained, with a yield of 97%. The colorless transparent liquid was a methyltin mercaptide derivative having a high boiling point.

Example 7

271.5 g of isooctyl mercaptopropionate was added to a reactor and stirred. 308 g of methyltin chloride aqueous solution comprising 15.0 wt. % of chloride was added dropwise. The pH value of the resulting mixture was regulated using aqueous ammonia to be between 3 and 5. The temperature was controlled at between 30 and 40° C. Thereafter, aqueous ammonia was further added dropwise to regulate the pH value to be 8, and thus the primary stage of the esterification occurred. The temperature was raised to between 50 and 70° C. for the secondary stage of the esterification. Thereafter, the mixture was allowed to stand until phases separated. The aqueous phase was removed. The organic phase was washed with 280 g of deionized water. The resulting solution was allowed to stand until phases separated. The obtained organic product was filtered, and evaporated under reduced pressure at a temperature of between 95 and 105° C. whereby removing water. Thus, 355 g of a colorless transparent liquid comprising 18.4 wt. % of tin was obtained, with a yield of 99%. The colorless transparent liquid was a methyltin mercaptide derivative having a high boiling point.

Example 8

Boiling points of the compounds prepared in Examples 1-7 were measured with the results as Table 1.

TABLE 1

| Example | Boiling point/° C. |
|---------|--------------------|
| 1 | 322.5 |
| 2 | 329.7 |
| 3 | 330.5 |
| 4 | 326.8 |
| 5 | 325.8 |
| 6 | 326.9 |
| 7 | 332.1 |

The measurement results showed that, the boiling points of the compounds exceed 320° C., which is 40° C. higher than that of conventional methyltin mercaptides.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing a compound of formula I or II,

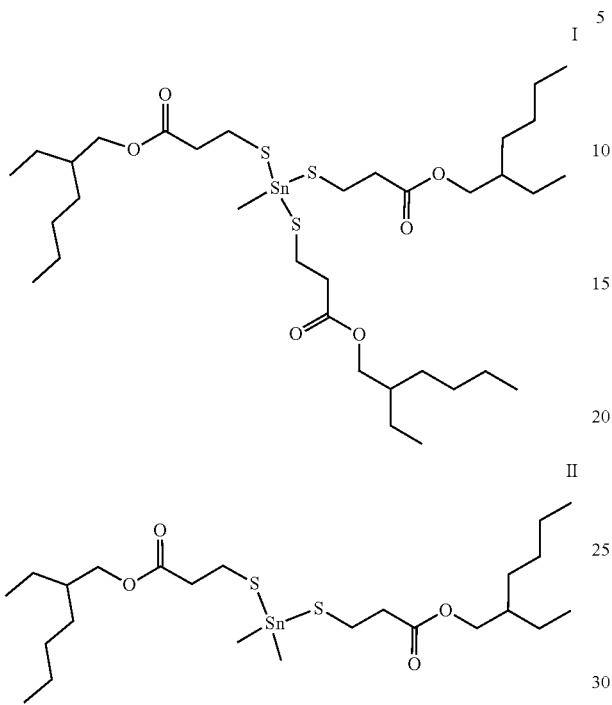

the method comprising the steps of:
a) adding isooctyl mercaptopropionate to a reactor, adding dropwise an aqueous solution of methyltin chloride, stirring and allowing for a complete reaction, and adding aqueous ammonia, an aqueous solution of sodium hydroxide, an aqueous solution of sodium bicarbonate, an aqueous solution of sodium carbonate, or a solution of an organic base to regulate the pH value of a resulting mixture from a starting value of between 2 and 8 to an end value of between 6 and 10 for a primary stage of esterification;
b) allowing a product obtained from step a) to proceed to a secondary stage of the esterification, allowing the product to stand until phases are separated, collecting and washing an organic phase using deionized water, allowing a resulting mixture to stand until phases are separated, and filtering; and
c) collecting an organic product obtained from step b), and evaporating the product under reduced pressure to yield the compound.

2. The method of claim 1, wherein in the primary stage of the esterification, a molar ratio of chloride in the methyltin chloride aqueous solution to the isooctyl mercaptopropionate is between 1:1.0 and 1:1.2.

3. The method of claim 1, wherein in the primary stage of the esterification, a reaction temperature is controlled at between 10 and 40° C.

4. The method of claim 1, wherein in the secondary stage of the esterification, a reaction temperature is controlled at between 40 and 80° C.

5. The method of claim 1, wherein a reaction temperature for the evaporation under reduced pressure is controlled at between 60 and 140° C.

* * * * *